US006865422B1

(12) United States Patent
Sloman et al.

(10) Patent No.: US 6,865,422 B1
(45) Date of Patent: Mar. 8, 2005

(54) CARDIAC STIMULATION METHOD AND ASSOCIATED SYSTEM USING A STIMULATION HISTOGRAM AS AN INTEGRITY DIAGNOSTIC TOOL TO MONITOR THE PERFORMANCE OF AUTOMATIC CAPTURE VERIFICATION

(75) Inventors: Laurence S. Sloman, Los Angeles, CA (US); Joseph J. Florio, La Canada, CA (US)

(73) Assignee: Pacesetter, Inc., Sylmar, CA (US)

( * ) Notice: Subject to any disclaimer, the term of this patent is extended or adjusted under 35 U.S.C. 154(b) by 410 days.

(21) Appl. No.: 09/964,225

(22) Filed: Sep. 25, 2001

(51) Int. Cl.[7] ............................................... A61N 1/365
(52) U.S. Cl. ........................................................ 607/28
(58) Field of Search .............................. 600/373, 374, 600/393, 509, 510, 519; 607/4, 5, 7, 9, 11, 27, 28

(56) References Cited

U.S. PATENT DOCUMENTS

| 4,513,743 | A | | 4/1985 | Van Arragon et al. | 128/419 PG |
|---|---|---|---|---|---|
| 5,088,488 | A | | 2/1992 | Markowitz et al. | ... 128/419 PG |
| 5,309,919 | A | | 5/1994 | Snell et al. | .................. 128/697 |
| 5,330,513 | A | | 7/1994 | Nichols et al. | ................ 607/32 |
| 6,456,882 | B1 | * | 9/2002 | Schloss | ........................ 607/28 |
| 6,584,355 | B2 | * | 6/2003 | Stessman | ...................... 607/29 |

* cited by examiner

*Primary Examiner*—Jeffrey R. Jastrzab
*Assistant Examiner*—Frances P. Oropeza

(57) ABSTRACT

An implantable cardiac stimulation device and method provide a histogram for storing the number of primary and backup stimulation pulses delivered at each amplitude setting, to monitor the performance of the automatic capture verification. The stimulation device delivers cardiac stimulation therapy in which a stimulation histogram advantageously stores the number of primary pulses delivered at each stimulation output, or range of outputs, and separately stores the number of high-energy backup stimulation pulses delivered. Knowing the historical frequency of the applied stimulation amplitudes is useful to a physician in selecting future stimulation pulse output settings and the working margin. This information is also useful in determining the expected remaining battery life. The stimulation histogram further provides a useful diagnostic tool for evaluating the integrity of the stimulation device, lead system and performance of the automatic capture algorithm.

26 Claims, 6 Drawing Sheets

CARDIAC STIMULATION METHOD AND ASSOCIATED SYSTEM USING A STIMULATION HISTOGRAM AS AN INTEGRITY DIAGNOSTIC TOOL TO MONITOR THE PERFORMANCE OF AUTOMATIC CAPTURE VERIFICATION

FIELD OF THE INVENTION

The present invention relates generally to an implantable cardiac stimulation device. More specifically, the present invention is directed to an implantable cardiac stimulation device that provides a histogram for storing the number of primary and backup stimulation pulses delivered at each amplitude setting, to monitor the performance of the automatic capture verification.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacing and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate. A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

A stimulation pulse delivered to the myocardium must be of sufficient energy to depolarize the tissue, thereby causing a contraction, a condition commonly known as "capture." In early pacemakers, a fixed, high-energy pacing pulse was delivered to ensure capture. While this approach is straightforward, it quickly depletes battery energy and can result in patient discomfort due to extraneous stimulation of surrounding skeletal muscle tissue.

The capture "treshold" is defined as the lowest stimulation pulse energy at which capture occurs. By stimulating the heart chambers at or just above threshold, comfortable and effective cardiac stimulation is provided without unnecessary depletion of battery energy. Threshold, however, is extremely variable from patient-to-patient due to variations in electrode systems used, electrode positioning, physiological and anatomical variations of the heart itself, and so on. Furthermore, threshold will vary over time within a patient as, for example, fibrotic encapsulation of the electrode occurs during the first few weeks after surgery. Fluctuations may even occur over the course of a day or with changes in medical therapy or disease state.

Hence, techniques for monitoring the cardiac activity following delivery of a stimulation pulse have been incorporated in modern pacemakers in order to verify that capture has indeed occurred. If a loss of capture is detected by such capture-verification algorithms, a threshold test is performed by the cardiac pacing device in order to re-determine the threshold and automatically adjust the stimulating pulse energy. This approach, called "automatic capture", improves the cardiac stimulation device performance in at least two ways: 1) by verifying that the stimulation pulse delivered to the patient's heart has been effective, and 2) greatly increasing the device's battery longevity by conserving the energy used to generate stimulation pulses.

Whenever a loss of capture is detected, a high-energy, safety, backup stimulation pulse is delivered to the heart within a short period of time, typically 60 to 100 ms, in order to provide backup support to the heart. The output of the primary stimulation pulse is then increased until capture is regained. Thereafter, an automatic threshold test is invoked in order to re-determine the minimum pulse energy required to capture the heart.

An exemplary automatic threshold determination procedure is performed by progressively decreasing the stimulation pulse amplitude from a functional output in small steps, for example 0.25 Volts, until capture is lost. The stimulation pulse amplitude is then increased in smaller increments, for example 0.125 Volts until capture is regained for two consecutive primary pulses. The output setting at which stable capture is regained is determined as the capture threshold. The stimulation pulse output is then adjusted to a setting equal to the threshold plus a working margin that allows small fluctuations in threshold to occur without frequent losses of capture.

The stimulation pulse amplitude will therefore be adjusted as fluctuations in threshold occur when automatic capture is enabled. Fluctuations in threshold can result from an instable electrode placement, a fracture of the conducting lead, or a discontinuity in the lead insulation. Fluctuations in threshold may also indicate a change in the patient's clinical condition.

It would be desirable to provide a diagnostic tool capable of distinguishing between safety backup pulses delivered at a high output setting from primary stimulation pulses delivered at the same high output setting. This information would be useful in assessing the performance of automatic capture verification by documenting how often safety, backup pulses are required. This information would also be valuable to a clinician in selecting programmed output settings and working margins. It would be desirable, therefore, to provide an implantable cardiac stimulation device and associated method capable of performing automatic capture verification with histogram storage of stimulation output for documenting not only the number of pulses delivered at each output setting but also the number of high-energy backup pulses.

SUMMARY OF THE INVENTION

The present invention addresses this need by providing an implantable cardiac stimulation device and associated method for counting and storing stimulation events according to pulse amplitude and according to whether the stimulation pulse was a primary pulse or a safety, backup pulse. The present invention further provides a method for displaying the stored data graphically on an external programmer.

Knowing the historical frequency of the applied stimulation amplitudes is useful to a physician in selecting future stimulation pulse output settings and the working margin. This information is also useful in determining the expected remaining battery life. A stimulation histogram further provides a useful diagnostic tool for evaluating the integrity of the stimulation device, lead system and performance of the automatic capture algorithm.

The foregoing and other features of the present invention are realized by providing an implantable cardiac stimulation device equipped with cardiac data acquisition capabilities. A preferred embodiment of the stimulation device includes a control system for controlling the operation of the device and executing various test algorithms; a set of leads for receiving cardiac signals and for delivering atrial and ventricular stimulation pulses; a set of sensing circuits comprised of sense amplifiers for sensing and amplifying the cardiac signals; and pulse generators for generating atrial and ventricular stimulation pulses. In addition, the device includes memory for storing operational parameters for the control system, and storing data such as a number of stimulation events within a stimulation histogram. The device also includes a telemetry circuit for communicating with an external programmer.

The present invention further provides an external programmer that preferably includes: a user interface, such as a keyboard, mouse or touch screen; a control system for controlling the operation of functions or tests carried out by the external programmer, a memory for storing control programs, operational parameters, or data received from the implantable device; and a display apparatus such as an LCD screen or printer. The external programmer also includes a telemetry unit for transmitting data to and from the implanted device.

In a preferred embodiment, histogram bins located in the device memory are used to store the number of stimulation pulses delivered to each chamber of the heart. Individual histogram bins are assigned to a stimulation output setting, preferably a pulse amplitude setting or a range of pulse amplitude settings. One histogram bin is assigned to store the number of safety, backup stimulation pulses delivered. The control system of the implanted device increments the count in the appropriate histogram bin each time a stimulation pulse is delivered. If more than one heart chamber or site is being stimulated with automatic capture, a set of histogram bins for counting the backup pulses and primary pulses is provided for each stimulated site. The data stored in the histogram bins may be downloaded to the external programmer and displayed graphically on a display screen or in a printed report.

The system and method of the present invention thus provide a valuable diagnostic tool for monitoring the performance of automatic capture by allowing the clinician to determine how many safety, backup pulses are delivered as opposed to primary pulses delivered at the same high-energy output.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout.

The present invention is directed at providing a stimulation histogram in an implantable cardiac stimulating device capable of delivering pacing therapy to one or more heart chambers, which may also be combined with cardioversion and defibrillation therapies. A general cardiac stimulation device will thus be described in conjunction with FIGS. 1 and 2 in which the stimulation histogram feature of the present invention could be implemented. It is recognized, however, that numerous variations of such a device exist in which the methods of the present invention could be implemented without deviating from the scope of the present invention.

Figure 1:
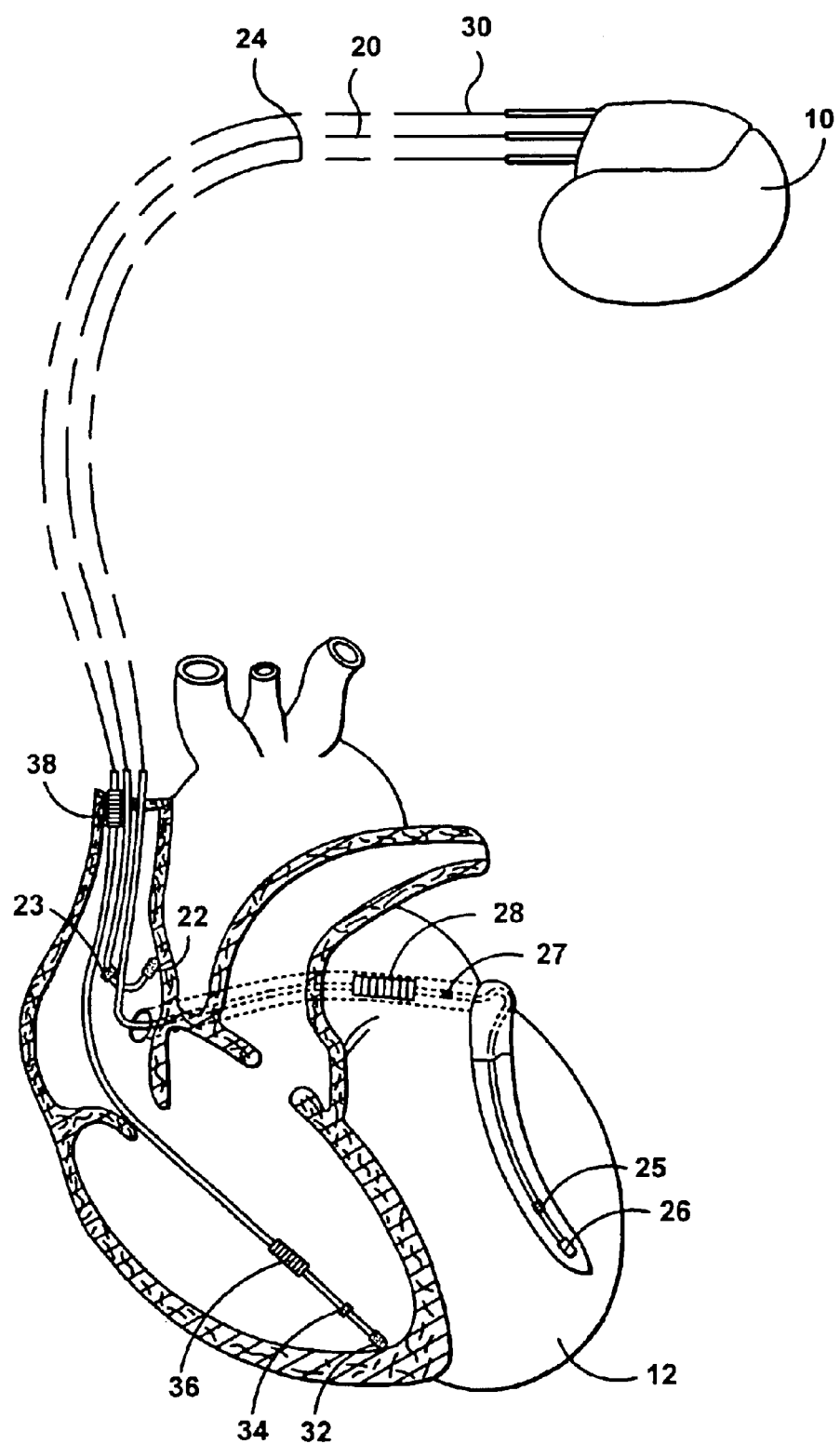
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode to adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
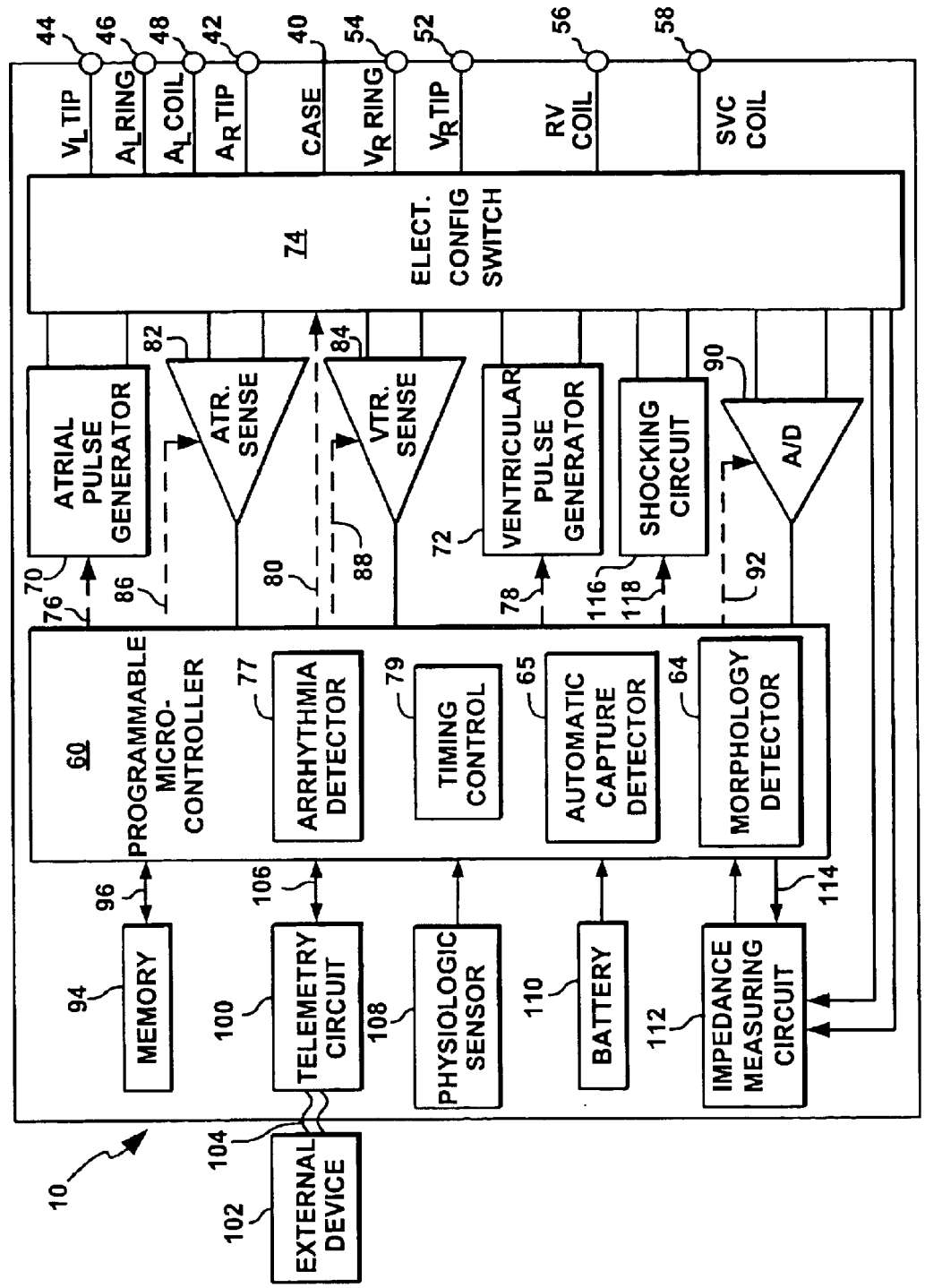
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often in referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The stimulation device 10 further includes a connector having a plurality of terminals 42, 43, 44, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal (AR TIP) 42 adapted for connection to the atrial tip electrode 22. The connector may also include a right atrial ring terminal (AR RING) 43 for connection to the atrial ring electrode 23.

To achieve left chamber sensing, pacing, and shocking, the connector includes at least a left ventricular tip terminal ($V_L$ TIP) 44, a left atrial ring terminal ($A_L$ RING) 46, and a left atrial shocking coil terminal ($A_L$ COIL) 48, which are adapted for connection to the left ventricular tip electrode 26, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g. unipolar, bipolar, cross-chamber, etc.) by selectively closing the appropriate combination of switches. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation; polarity.

Stimulation during pacing can be performed in a bipolar mode in devices combining pacing and cardioversion/defibrillation functions because unipolar simulation may interfere with arrhythmia detection. Hence, in one embodiment of the present invention, the switch bank 74 is configured such that right atrial pacing and sensing is performed in a bipolar fashion between the right atrial tip electrode 22 and right atrial ring electrode 23; right ventricular pacing and sensing is performed in a bipolar fashion between right ventricular tip electrode 32 and right ventricular ring electrode 34; and left ventricular pacing and sensing is performed in a bipolar fashion between coronary sinus tip electrode 26 and the coronary sinus ring electrode 27.

Right ventricular sensing may alternatively be configured between the right ventricular coil electrode 36 and the right ventricular ring electrode 34. Bipolar sensing may also be achieved using an integrated bipolar lead wherein the right ventricular coil electrode 36 and right ventricular ring electrode 34 are electrically coupled within the right ventricular lead body 30. Bipolar sensing is then performed between the right ventricular tip electrode 32 and the coupled right ventricular coil electrode 36 and right ventricular ring electrode 34.

Any electrode combination that allows acceptable stimulation and sensing thresholds may be used. By employing the right ventricular coil electrode 36, possibly in combination with right ventricular ring electrode 34, the electrode surface during sensing is increased, advantageously reducing the effects of lead polarization. Other techniques of reducing lead polarization such as titanium nitride coating may also be used to improve the operation of the present invention.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation. The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (AD) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". When automatic capture is enabled, the microcontroller 60 searches for a depolarization signal following a stimulation pulse during an "detection window" set by timing control circuitry 79 within microcontroller 60.

The microcontroller 60 enables the data acquisition system 90 via control signal 92 to sample the cardiac signal that falls in the capture detection window. The sampled signal is evaluated to determine if it is an evoked response signal based on its amplitude, peak slope, or another signal feature or combination of features. The detection of an evoked response during the detection window indicates that capture has occurred.

Capture detection may occur on a beat-by-beat basis or on a sampled basis. When loss of capture is detected, a safety, backup pulse is delivered shortly after the primary pulse in order to prevent asystole. Preferably, a capture threshold search is then performed in order to re-determine the threshold and appropriately adjust the stimulation pulse output. A capture threshold search may also be performed on a periodic basis, preferably once a day during at least the acute phase (e.g., the first 30 days) and less frequently thereafter. A capture threshold search would begin at a desired starting point (either a high output level or the level at; which capture is currently occurring) and continue by decreasing the output level until capture is lost. The output level is then increased again until capture is regained. The lowest output level at which sustained capture is regained is known as the capture threshold. Thereafter, the stimulation output is adjusted to a level equal to the capture threshold plus a working margin.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patients heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104. In accordance with the present invention, diagnostic data stored in memory 94, such as data stored in a stimulation histogram, may also be sent to the external device 102 through communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, V-V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 µA, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 which is enabled by the microcontroller 60 by means of a control signal 114.

It is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
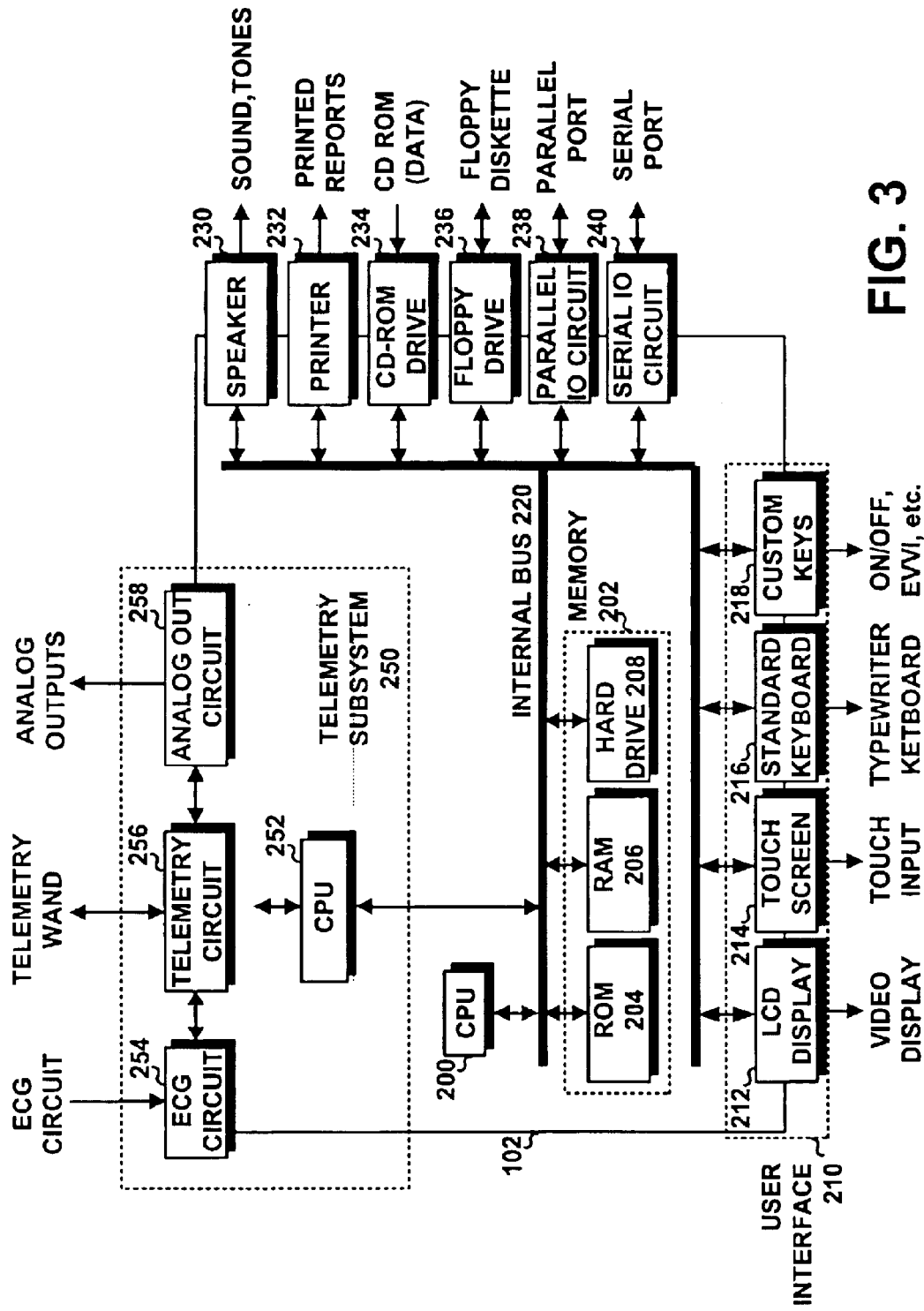
FIG. 3 is a functional block diagram illustrating the basic elements of an external device that can send and receive commands or data through telemetric communication with the stimulation device of FIG. 2.

FIG. 3 illustrates a simplified block diagram of the external programming device 102 that communicates with device 10 through a telemetry circuit 100. The external device 102 possesses a central processing unit (CPU) 200 that controls the operations carried out by the external device 102 such as programming the operating parameters of device 10 or carrying out various testing or diagnostic functions. Testing, and diagnostic functions preferably include evoked response sensitivity testing, and may also include algorithms for non-invasive programmed stimulation for arrhythmia induction, arrhythmia detection and termination testing, threshold testing, lead impedance measurements, etc.

CPU 200 is in communication with a memory 202 via internal bus 220. The memory 202 may include a read-only memory (ROM) 204, a random access memory (RAM) 206, and hard drive 208. Operating parameters and algorithms controlling the programming and testing functions carried out by the external device 102 may be stored in memory 202 and accessed by CPU 200. External device 102 is equipped with an user interface 210 that allows connection to an LCD display 212, a touch screen 214, a key board 216, and custom keys 218 that control a specific function or deliver a specific command automatically. Each component of the user interface 212 is also in communication with the CPU 200 and memory 202 via the internal bus 220 to allow user input, such as programming commands delivered using the touch screen 214, keyboard 216, or custom keys 218, to be received by the CPU 200 and/or stored in memory 202. Programming selections made by a user and results of programming or testing operations may be displayed on the LCD display 212. Messages relating to the success of the programming command, recommended programmed settings, or warnings to the user regarding selected parameters may also be displayed on the LCD display 212.

The CPU 200 and memory 202 are also in communication with various input/output interfaces via the internal bus 220 that may include: a speaker 230 for delivering sounds or tones during the programming procedures; a printer 232 for printing results of programming or testing operations; a CD-ROM drive 234 and floppy drive 236 to which data from testing or programming operations may be written; and a parallel input/output port 238 and a serial input/output port 240 to allow connection to auxiliary equipment.

The external device 102 is further equipped with a telemetry subsystem 250. The telemetry subsystem 250 includes a central processing unit (CPU) 252 for controlling the transfer of data between the external device 102 and the implanted device 10. Thus the telemetry CPU 252 is in communication with the internal bus 220 so that data may be transferred between the telemetry subsystem 250 the CPU 200, memory 202, user interface 210, and other input/output interfaces, 230, 232, 234, 236, 238, and 240. The telemetry CPU 252 is connected to at least three interfaces which facilitate the receipt or transmission of data. An ECG circuit interface 254 allows connection to surface ECG leads for collecting a patient's ECG. The ECG may be displayed in real time on the video display 212. A telemetry circuit interface 256 allows connection to a telemetry wand that is placed over the implanted device 10 for receiving or sending data such as cardiac signal data stored in the memory 94 of device 10 or programmed operating parameters received at the user interface 210. An analog output circuit interface 258 allows connection to it, an analog output port.

Figure 4:
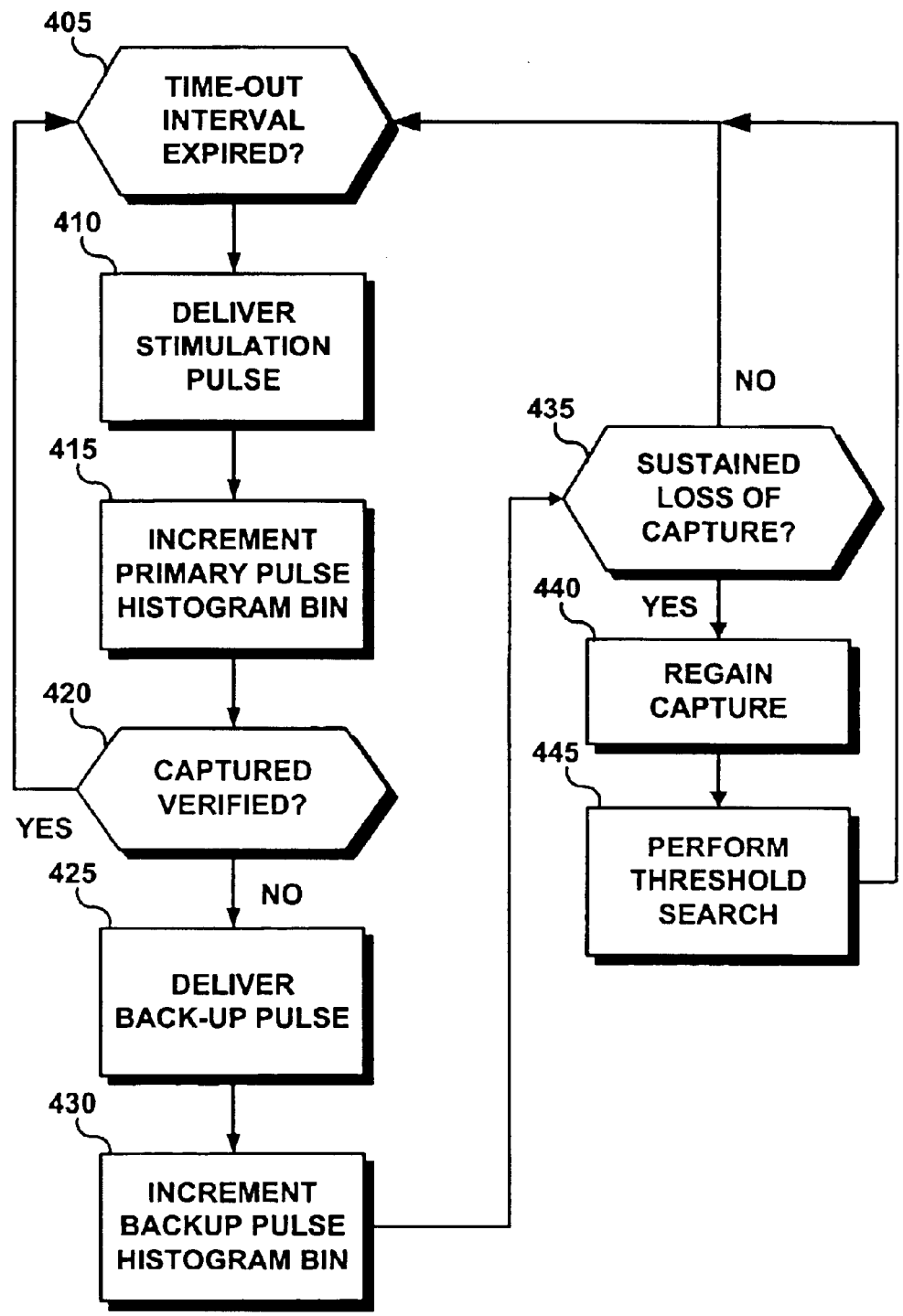
FIG. 4 is a flow chart providing an overview of the operations included in one embodiment of the present invention for storing data in a stimulation histogram.

In FIG. 4, a flow chart is shown describing an overview of the operation implemented in one embodiment of the device 10 for storing a stimulation histogram. In this flow chart, the various algorithmic steps are summarized in individual "blocks". Such blocks describe specific actions or decisions that must be made or carried out as the algorithm proceeds. Where a microcontroller (or equivalent) is employed, the flow chart presented herein provides the basis for a "control program" that may be used by such a microcontroller (or equivalent) to effectuate the desired control of the stimulation device. Those skilled in the art may readily write such a control program based on the flow chart and other descriptions presented herein.

At step 405, the microcontroller 60 waits for a time-out interval, for example an atrial escape interval, a ventricular escape interval, or an atrial-ventricular (AV) delay, to expire, as controlled by timing control circuitry 79. Upon expiration of the time-out interval, the device 10 will generate a stimulation pulse to be delivered at step 410 by the appropriate atrial or ventricular pulse generator, 70 or 72 respectively.

At step 415, the microcontroller 60 increments a counter in a primary pulse histogram bin. The microcontroller 60 first selects the histogram bin corresponding to the stimulation pulse output (amplitude or width) at which the primary stimulation pulse was delivered. Histogram bins may be assigned to a specific pulse output setting or a range of pulse output settings. The output setting or settings assigned to a histogram bin may be predefined and stored in memory 90. These assignments may also be programmable by the user, with the programmed number of histogram bins and the corresponding output setting(s) stored in memory 90.

At decision step 420, the automatic capture verification algorithm of device 10 is executed by microcontroller 60 to verify that the primary stimulation pulse has indeed captured the stimulated heart chamber. If capture is verified, various timers are reset in timing control circuitry 79, and device 10 returns to step 405 to wait for the next time-out interval to expire.

However, if at decision step 420 the automatic capture verification algorithm has not captured the stimulated heart chamber, i.e., loss of capture is detected, a high-energy backup stimulation pulse is delivered at step 425. At step 430, the microcontroller 60 increments a histogram bin assigned exclusively to backup stimulation pulses. The backup stimulation pulse is typically delivered at a high pulse amplitude, e.g. 5 Volts. Primary pulses may also be delivered at 5 V, or another pulse output setting equal to the backup pulse output. However, the number of primary pulses delivered at the same high-output setting as backup pulses are stored in a separate, backup pulse histogram bin.

At step 435, the microcontroller 60 determines if a sustained loss of capture has occurred, typically defined as two consecutive losses of capture, and, if so, it increases the primary pulse output until capture is regained at step 440. A threshold search is performed at step 445 to re-determine the capture threshold and appropriately adjust the pulse output. The device 10 then returns to step 405. Test stimulation pulses and backup stimulation pulses that are delivered during the threshold search are preferably not counted in the histogram bins.

If more than one heart chamber is being stimulated with capture automatically verified, then a separate set of histogram bins may be assigned to each chamber or each stimulation site. For example, in the embodiment shown in FIG. 1, primary pulse histogram bins and backup pulse histogram bins may be assigned to each of the right atrium, left atrium, right ventricle and left ventricle (or to each stimulation site in or for each chamber). Each histogram bin may contain a number of counters assigned to a number of output settings as appropriate for the particular stimulation site.

At any time, a clinician may observe the contents of the stimulation histogram bins by providing a command to device 10 using the external programmer 102 to download the data to the external programmer 102. The contents of the stimulation histogram bins are preferably displayed graphically on LCD display 212. After the data is downloaded, the clinician may choose to clear the stimulation histogram bins so that the counts of primary and backup stimulation pulses will begin again from zero.

Figure 5:
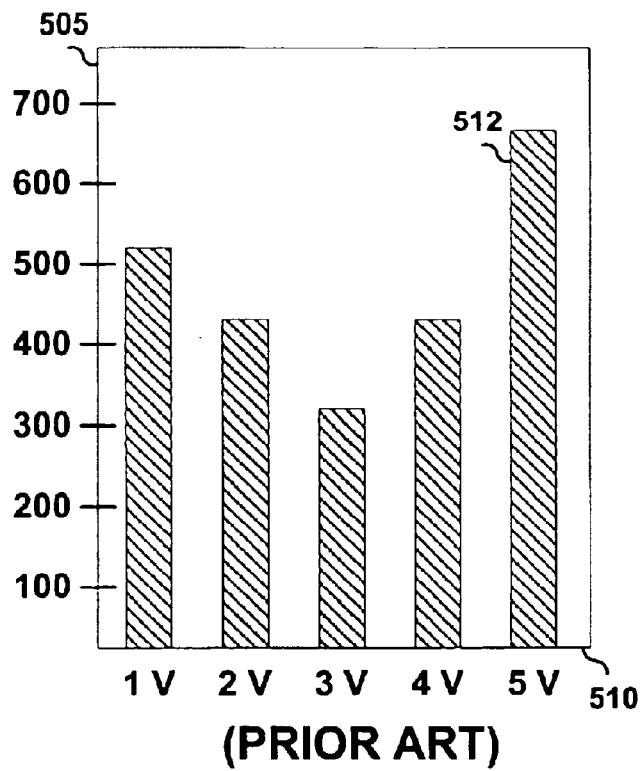
FIG. 5 is an illustration of a graphical display of stimulation histogram data created using a conventional stimulation device.

In FIG. 5, a graphical depiction of a stimulation histogram is shown as it might be displayed according to known or available methods. The number of stimulation pulses is plotted along the y-axis 505. The pulse output is plotted along the x-axis 510. In this example, the bar 512 representing the number of pulses delivered at the highest setting, 5 V, includes both primary pulses and backup pulses. However, the clinician has no way of distinguishing, from this histogram, how many backup pulses were in fact delivered, and therefore cannot discern how many times loss of capture occurred. Nor can the clinician determine if this high output setting was required for the delivery primary stimulation pulses due to an increased capture threshold.

Figure 6:
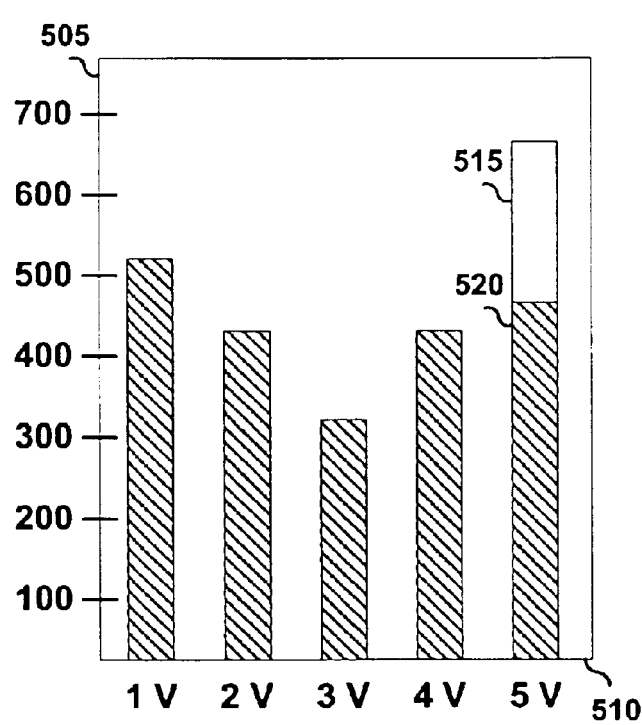
FIG. 6 is an illustration of a graphical display of stimulation histogram data created using the methods of FIG. 4.

In FIG. 6 a graphical depiction of a stimulation histogram displayed according to one embodiment of the present invention is shown. The number of backup stimulation pulses delivered at 5 V is represented by the white bar 515. The cross-hatched bar 520 represents the number of primary stimulation pulses delivered at 5 V.

Figure 7:
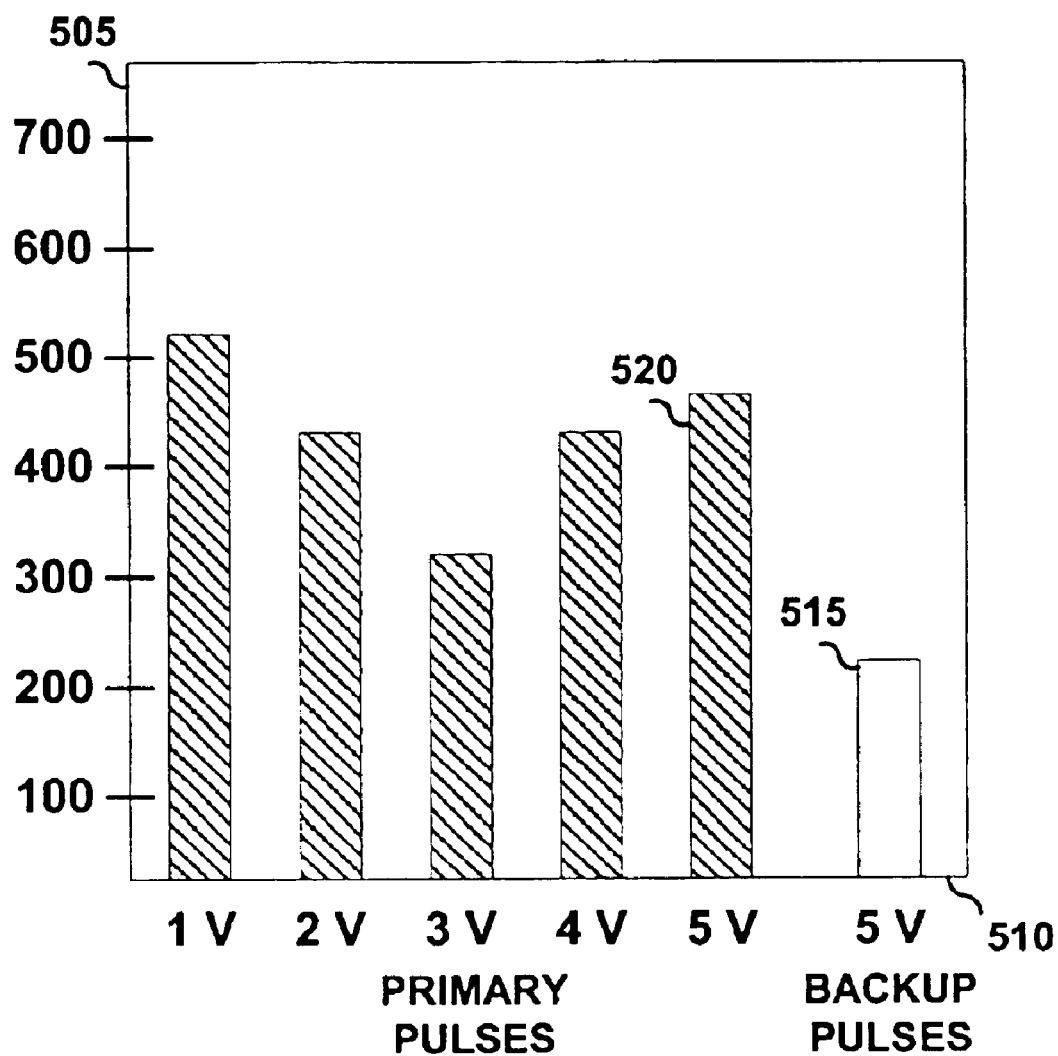
FIG. 7 is an alternative illustration of a graphical display of stimulation histogram data created using the methods of FIG. 4.

Alternatively, the stimulation histogram data stored according to methods included in the present invention may be displayed as shown in FIG. 7. In this display, the white histogram bar 515 representing the backup stimulation pulses is plotted separately along the x-axis 510 from the cross-hatched histogram bars representing the primary stimulation pulses.

In either display depicted in FIG. 6 or 7, the number of times a safety backup stimulation pulse required can easily be interpreted by a user. This information is useful in assessing the performance of automatic capture verification as well as in selecting future programmed output settings.

Thus, a method and apparatus have been described for delivering cardiac stimulation therapy in which a stimulation histogram advantageously stores the number of primary pulses delivered at each stimulation output, or range of outputs, and separately stores the number of high-energy backup stimulation pulses delivered. While detailed descriptions of specific embodiments of the present invention have been provided, it would be apparent to those reasonably skilled in the art that numerous variations of acquiring, storing, and displaying a stimulation are possible in which the concepts and methods of the present invention may readily be applied. As an example, the stored number of backup stimulation pulses can be automatically compared to the stored number of primary stimulation pulses, to evaluate the performance of the automatic capture verification feature based on a historical frequency of occurrence of the primary stimulation pulses and the backup stimulation pulses. The descriptions provided herein, therefore, are for the sake of illustration and are not intended to be exclusive.

What is claimed is:

1. A method of monitoring the performance of an automatic capture verification feature in a cardiac stimulation device, the method comprising:
    monitoring the number of backup stimulation pulses delivered at a high-energy output setting, and storing the number of backup stimulation pulses delivered at the high-energy output setting;
    monitoring the number of primary stimulation pulses delivered at each of a plurality of stimulation output settings, and storing the number of primary stimulation pulses at the respective output settings;
    wherein at least one of the plurality of stimulation output settings of the primary stimulation pulses is at the high-energy output setting; and
    comparing the stored number of backup stimulation pulses to the stored number of primary stimulation pulses to evaluate the performance of the automatic capture verification feature;
    wherein the step of comparing the stored number of backup stimulation pulses to the stored number of primary stimulation pulses comprises selectively comparing the number of backup stimulation pulses delivered at the high-energy output setting with the number of primary stimulation pulses delivered at the high-energy output setting.

2. The method of claim 1, further comprising the step of selecting a stimulation pulse output setting based on the historical frequency of occurrence of the primary stimulation pulses and the backup stimulation pulses.

3. The method of claim 2, wherein the step of storing the number of backup stimulation pulses comprises storing the number of the backup stimulation pulses in a first histogram bin assigned to the high-energy output getting.

4. The method of claim 3, wherein the step of storing the number of primary stimulation pulses comprises storing the number of the primary stimulation pulses in a second histogram bin.

5. The method of claim 4, further comprising graphically displaying the first histogram and the second histogram.

6. The method of claim 1, further comprising the step of determining an expected remaining life of a power source based on a historical frequency of occurrence of the primary stimulation pulses and the backup stimulation pulses.

7. The method of claim 1, further comprising the step of evaluating the integrity of the stimulation device based on a historical frequency of occurrence of the primary stimulation pulses and the backup stimulation pulses.

8. The method of claim 1, wherein the step of storing the number of backup stimulation pulses comprises the step of storing the number of backup stimulation pulses delivered to each cardiac chamber.

9. The method of claim 8, wherein the step of storing the number of backup stimulation pulses comprises the step of storing the number of backup stimulation pulses delivered to each stimulation site.

10. The method of claim 9, wherein the step of storing the number of backup stimulation pulses comprises the step of storing the number of backup stimulation pulses delivered to each stimulation site in at least one cardiac chamber.

11. A stimulation device that monitors the performance of an automatic capture verification feature, comprising:
    a pulse generator that selectively generates backup stimulation pulses at a high-energy output setting and primary stimulation pulses at each of plurality of stimulation cutout settings;
    wherein at least one of the plurality of stimulation output settings of the primary stimulation pulses is at the high-energy output setting;
    a memory that stores the number of backup stimulation pulses at the high-energy output setting and stores the number of primary stimulation pulses delivered at each of a plurality of stimulation output settings;
    a counter that increments the stored number of backup stimulation pulses stored in the memory, wherein the counter further increments the stored number of primary stimulation pulses when a primary stimulation pulse is delivered at a given output setting; and
    a controller that is operative to compare the stored number of backup stimulation pulses to the stored number of primary stimulation pulses to allow for an evaluation of the performance of the automatic capture verification feature;
    wherein the controller is operative to selectively compare the number of backup stimulation pulses delivered at the high-energy output setting with the number of primary stimulation pulses delivered at the high-energy output setting.

12. The stimulation device of claim 11, wherein the memory stores the number of occurrences of the backup stimulation pulses in a histogram bin assigned to the high-energy output setting.

13. The stimulation device of claim 12, wherein the counter increments the histogram bin each time a backup stimulation pulse is delivered at the high-energy output setting in response to loss of capture.

14. The stimulation device of claim 13, wherein the memory stores the number of occurrences of the primary stimulation pulses in a plurality of histogram bins each assigned to a stimulation output setting.

15. The stimulation device of claim 14, wherein the memory stores the number of the primary stimulation pulses in a plurality of histogram bins each assigned to a range of stimulation output settings.

16. The stimulation device of claim 11, wherein the counter stores the number of the primary stimulation pulses in one of the plurality of histogram bins, each time a primary stimulation pulse is delivered at the given output setting.

17. The stimulation device of claim 11, wherein the memory stores, in a first histogram, the number of backup stimulation pulses delivered to each stimulated cardiac chamber.

18. The stimulation device of claim 17, wherein the memory stores, in a second histogram, the number of primary stimulation pulses delivered at the plurality of stimulation output settings delivered to each stimulated cardiac chamber.

19. A stimulation device that monitors the performance of an automatic capture verification feature, comprising:
    means for storing a number of backup stimulation pulses delivered at a high-energy output setting by the device;
    means for incrementing the stored number of backup stimulation pulses delivered at the high-energy output setting;
    means for storing a number of primary stimulation pulses delivered at each of a plurality of stimulation output settings;
    wherein at least one of the plurality of stimulation output settings of the primary stimulation pulses is at the high-energy output setting;
    means for incrementing the stored number of primary stimulation pulses at the respective output settings; and
    means for comparing the stored number of backup stimulation pulses to the stored number of primary stimulation pulses to evaluate the performance of the automatic capture verification feature;
    wherein the means for comparing the stored number of backup stimulation pulses to the stored number of primary stimulation pulses comprises selectively comparing the stored number of backup stimulation pulses delivered at the high-energy output setting with the stored number of primary stimulation pulses delivered at the high-energy output setting.

20. The stimulation device of claim 19, wherein the means for storing a number of backup stimulation pulses comprises storing the number of occurrences of the backup simulation pulses in a histogram bin assigned to the high-energy output setting.

21. The stimulation device of claim 20, wherein the incrementing means increments the histogram bin each time a backup stimulation pulse is delivered at the high-energy output setting in response to loss of capture.

22. The stimulation device of claim 21, wherein the means for storing a number of primary stimulation pulses comprises storing the number of occurrences of the primary stimulation pulses in a plurality of histogram bins each assigned to a stimulation output setting.

23. The stimulation device of claim 22, wherein the means for storing a number of primary stimulation pulses comprises storing the number of the primary stimulation pulses in a plurality of histogram bins each assigned to a range of stimulation output settings.

24. The stimulation device of claim 23, wherein the incrementing means stores the number of the primary stimulation pulses in one of the plurality of histogram bins, each time a primary stimulation pulse is delivered at the given output setting.

25. The stimulation device of claim 19, wherein the means for storing a number of backup stimulation pulses comprises storing, in a first histogram, the number of backup stimulation pulses delivered to each stimulated cardiac chamber.

26. The stimulation device of claim 25, wherein the means for storing a number of primary stimulation pulses comprises storing, in a second histogram, the number of primary stimulation pulses delivered at the plurality of stimulation output settings delivered to each stimulated cardiac chamber.

* * * * *